US007262305B2

(12) United States Patent
Dutova et al.

(10) Patent No.: US 7,262,305 B2
(45) Date of Patent: Aug. 28, 2007

(54) ANISOTROPIC FILMS BASED ON 1,8-NAPHTHOYLENE-1',2'-BENZIMIDAZOLE SULFONATES AND LYOTROPIC LIQUID CRYSTAL SYSTEMS AND METHODS FOR MAKING

(75) Inventors: Tatyana Ya. Dutova, Moscow (RU); Elena N. Sidorenko, Moscow (RU)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 11/212,825

(22) Filed: Aug. 25, 2005

(65) Prior Publication Data

US 2006/0062932 A1    Mar. 23, 2006

Related U.S. Application Data

(62) Division of application No. 10/601,238, filed on Jun. 20, 2003, now Pat. No. 7,026,019.

(30) Foreign Application Priority Data

Jun. 28, 2002    (RU) ............................. 2002117253

(51) Int. Cl.
 *C07D 235/04*  (2006.01)
 *C09K 19/52*  (2006.01)
(52) U.S. Cl. ................ 548/301.7; 252/299.01
(58) Field of Classification Search ........... 252/299.01; 544/339, 342; 548/301.7
See application file for complete search history.

(56) References Cited

U.S. PATENT DOCUMENTS

| 2,553,961 A | 5/1951 | Dreyer |
| 2,949,467 A | 8/1960 | Staeuble |
| 4,024,144 A | 5/1977 | Groll et al. |
| 4,588,517 A | 5/1986 | Kaneko et al. |
| 5,470,921 A | 11/1995 | Kaul et al. |
| 6,583,284 B1 * | 6/2003 | Sidorenko et al. ........... 544/342 |
| 7,026,019 B2 * | 4/2006 | Dutova et al. ................ 428/1.1 |
| 7,045,177 B2 * | 5/2006 | Dutova et al. ................ 428/1.1 |

FOREIGN PATENT DOCUMENTS

| EP | 0961138 A1 | 12/1999 |
| EP | 1128192 A1 | 8/2001 |
| JP | 51-111237 | 10/1976 |
| JP | 52-72726 | 6/1977 |
| JP | 52-72726 | * 6/1997 |
| WO | WO94/28073 | 12/1994 |

OTHER PUBLICATIONS

Derwent abstract for JP 52-72726.*
CAPLUS 2002: 982688.*
Derwent abstract for JP 51-111237, 1976.
Derwent abstract for JP 52-72726, 1976.
Leonid Ya Ignatov, et al., "Thin Crystal Film Polarizers and Retarders", Liquid crystal Materials, Devices, and Applications VIII, Proceedings of SPIE. vol. 4658 (2002), pp. 79-89.
John Lydon, "Chapter XVIII Chromonics", pp. 981-1007, Handbook of Lipped Crystals. vol. 2B 1978.
P. Lazarev, M. Paukshto, "Thin Crystal Film Retarders", IDW'00 Conference Proceedings, Dec. 2000, Japan, 2 pages.
D. Tocksteinova, J. Slosar, J. Urbanek and J. Chura {hacek over (c)} ek, "New Fluorescence Reagents for Indentification of Organic Substances. II", Mikrochimica Acta [Wien] 1979 II, pp. 193-199, (German Publication with English summary).
Pavel Lazarev, Natalya Ovchinnikova, and Michael Paukshto, "P-6: Submicron Thin Retardation Coating", SID 01 Digest, pp. 1-3.

* cited by examiner

*Primary Examiner*—Shean C. Wu
(74) *Attorney, Agent, or Firm*—Westerman, Hattori, Daniels & Adrian, LLP.

(57) ABSTRACT

Optically anisotropic films based on sulfoderivatives of 1,8-naphthoylene-1',2'-benzimidazole are disclosed. These compounds form stable lyotropic liquid crystal systems that exhibit excellent optical properties with films that are significantly thinner that the current state of the art. The lyotropic liquid crystal systems may be deposited on substrates for use in a wide variety of commercial applications.

4 Claims, 3 Drawing Sheets

US 7,262,305 B2

ANISOTROPIC FILMS BASED ON 1,8-NAPHTHOYLENE-1',2'-BENZIMIDAZOLE SULFONATES AND LYOTROPIC LIQUID CRYSTAL SYSTEMS AND METHODS FOR MAKING

RELATED APPLICATIONS

This application is a divisional of U.S. patent application Ser. No. 10/601,238 filed Jun. 20, 2003, now U.S. Pat. No. 7,026,019 which claims priority to Russian Patent Application Serial No. 2002117253, filed on Jun. 28, 2002, the disclosures of which are hereby incorporated by reference in their entirety.

FIELD OF THE INVENTION

The present invention relates generally to the fields of organic chemistry, more specifically to the synthesis of sulfoderivatives (sulfonates) of heterocyclic compounds, and optically anisotropic films based on these compounds.

BACKGROUND OF THE INVENTION

Progress in modern technologies is based on creating new materials and developing optical elements with desired properties based thereupon. In particular, a necessary element in the design of modem displays is an optically anisotropic film possessing the optimum combination of characteristics for a given application.

A number of polymeric materials may be employed in the manufacture of optically anisotropic films. The anisotropic optical properties of these films result from uniaxial extension and modification with organic or inorganic (iodine) compounds. Poly-vinyl alcohol, (PVA) is commonly used as the base polymer as described in *Liquid Crystals: Applications and Use*, B. Bahadur (ed.), World Scientific, Singapore (1990), Vol. 1, p. 101–103. However, the low thermal stability of PVA-based films limits their applicability. New methods for the synthesis of optically anisotropic films possessing improved characteristics are needed for these reasons.

Organic dichroic dyes may be used for the synthesis of optically anisotropic films that exhibit excellent optical and workability characteristics. Films based on such compounds are obtained through application of a liquid-crystalline aqueous dye solution onto a substrate surface, followed by evaporation of the solvent, such as for instance water. Anisotropic properties may be imparted to the films either through preliminary mechanical orientation of the substrate surface, such as is described in U.S. Pat. No. 2,553,961, or by means of an external orienting action, such as for example mechanical, electromagnetic, or the like, exerted on the film material while it is in a liquid crystal state. This approach is explained in greater detail in PCT patent publication WO 94/28073.

Although the liquid-crystalline properties of dye solutions have been known for some time, extensive investigations of these systems have begun only recently. The new research efforts have been stimulated by the capability of some of these dyes of forming "chromonic" liquid crystal systems. A distinctive feature of chromonic systems is that dye molecules are packed into supramolecular complexes having the form of columns, which are the structural elements of a mesophase. The highly ordered structure of dye molecules in these columns allows use of these mesophases for forming strongly dichroic oriented films.

Molecular structures, phase diagrams, and the mechanisms of molecular aggregation in various chromonic systems, including organic dyes, have been previously reviewed (i.e. Lydon, J. Chromonics, in: *Handbook of Liquid Crystals* (Wiley-VCH, Weinheim, 1998), Vol. 2B, pp. 981–1007). A special feature of dye molecules that form chromonic mesophases is the presence of peripheral groups that render these dyes water-soluble. The main structural unit of all chromonic mesophases is a column of stacked molecules. The chromonic mesophases of organic dyes are soluble, possess a special structure, and are characterized by specific phase diagrams and optical properties.

By using dichroic dyes capable of forming lyotropic liquid crystal (LLC) systems, it is possible to obtain films possessing a high degree of optical anisotropy. Such films exhibit the properties of E-type polarizers, related to peculiarities of the optical absorption of the chromonic supramolecular complexes. These films behave as retarders (phase-shifting devices) in the spectral regions where the absorption is absent. The phase-shifting properties of these anisotropic films are related to their birefringence which is a difference in refractive indices measured in the direction of application of the liquid-crystalline solution onto a substrate and in the perpendicular direction. These properties of LLC systems account for the growing interest in these materials. New methods are under development to obtain films based on such organic dyes. Recent progress has included both optimization of the film application conditions and identification of new LLC compositions. In particular, new LLC compounds for the synthesis of optically anisotropic films may be obtained by introducing modifiers, stabilizers, surfactants, and other additives into the known compositions so as to improve characteristics of the films. More detailed discussions of these processes are provided in Russian Patent RU 2047643 and published PCT patent application WO 99/31535.

In recent years, the demand for optically anisotropic films characterized by selectivity with respect to various wavelength has increased. Because of the need for films with maximum absorption that may be varied throughout a broad spectral range, from the infrared (IR) to the ultraviolet (UV), there is a strong desire for a broad assortment of compounds capable of forming LLC phases and films possessing required properties. In this context, increased attention has been directed to birefringent film (retarders) materials that are applicable for liquid crystal displays and telecommunication lines. Additional background information on these topics is available in Yeh, P. *Optical Waves in Layered Media*, (John Wiley & Sons, New York, 1998); and in Yeh, P. and Gu, C. *Optics in Liquid Crystal Displays* (John Wiley & Sons, New York, 1999). Ultrathin birefringent films can be obtained by forming optically anisotropic layers of liquid crystal systems based on organic dyes. This process has been described in P. Lazarev and M. Paukshto, "Thin Crystal Film Retarders" (2000), *Proceeding of the 7th International Display Workshop on Materials and Components* (Kobe, Japan, November 29–December 1), pp. 1159–1160, wherein thin optically anisotropic crystalline films based on disulfonic acid esters of Vat Red 14 dye were obtained. The films included a mixture of cis- and trans-isomers of naphthalenecarboxylic acid dibenzimidazoles with the following structural formulas:

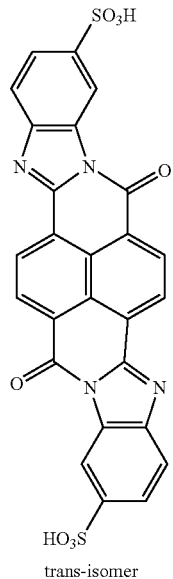

trans-isomer

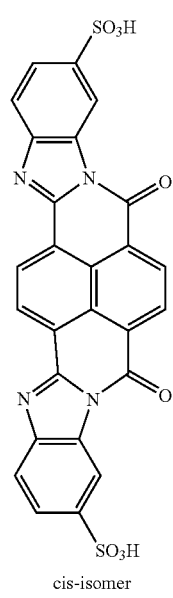

cis-isomer

Using this technology, it is possible to control the crystallographic axis direction in the film in the course of application and crystallization on a substrate. The films, obtained on glass plates with dimensions 5 by 7.5 cm, possessed homogeneous composition and high crystalline order and were characterized by a dichroic ratio $K_d$ equal to 28. Such films can be used as polarizers and retarders.

As FIG. 1 shows, the oriented films based on Vat Red 14 dye exhibit a high degree of optical anisotropy, as characterized by a large difference of the refractive indices for the ordinary and extraordinary rays: $n_o - n_e = 0.6$–$0.8$ for $l = 550$–$700$ nm. Use of these films as retarders is restricted to a green spectral range, where the dye does not absorb light.

Thin birefringent films that are transparent in the visible range may also be based on disodium chromoglycate (DSCG), a compound with the structural formula:

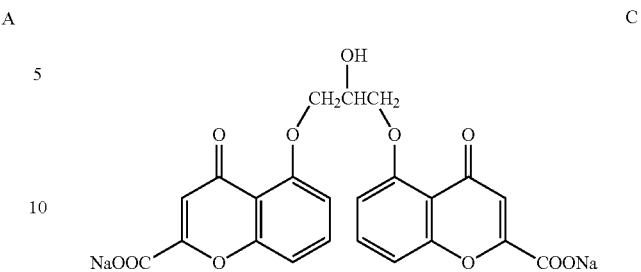

The degree of optical anisotropy of an oriented film of this compound is not as large. The difference of the refractive indices amounts to approximately 0.1–0.13. However, since the thickness of DSCG layers can be varied within broad limits, it is possible to achieve a desired phase shift even with this relatively low. The main disadvantage of DSCG films is their temporal instability, which is manifested by gradual recrystallization and a decrease in the degree of optical anisotropy.

Various compositions based on water-soluble organic dyes can be also used for obtaining optically anisotropic films according to the above technology as illustrated in PCT publications WO 94/28073 and WO 99/31535, However, a common disadvantage of these materials is high absorption in the visible spectral range. This property significantly restricts the use of these dyes for the synthesis of transparent birefringent films.

SUMMARY OF THE INVENTION

In one embodiment of the present invention, 1,8-Naphthoylene-1',2'-benzimidazole sulfoderivatives of the general structural formula

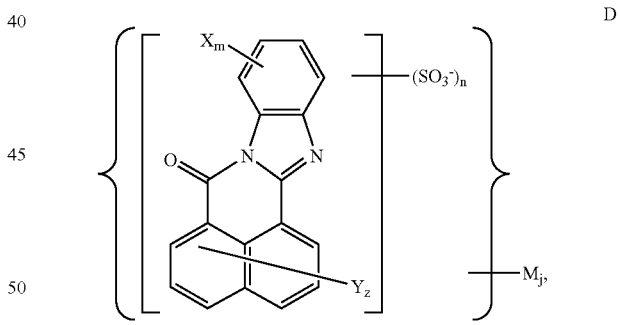

are provided. In compound, n is an integer in the range of 1 to 4, m is an integer in the range from 0 to 4; z is an integer in the range of 0 to 6, and the values of m, n, and z satisfy the equation $m+z+n \leq 10$. X and Y are individually selected from the group consisting of $CH_3$, $C_2H_5$, $OCH_3$, $OC_2H_5$, Cl, Br, OH, and $NH_2$. M is a counterion and j is the number of different counterions (M) in a single molecule of said 1,8-Naphthoylene-1',2'-benzimidazole sulfoderivative.

In a further embodiment of the present invention, 1,8-Naphthoylene-1',2'-benzimidazole sulfoderivatives are provided wherein the structural formula is chosen from the group consisting of structures I–VIII, wherein X and Y are individually selected from the group consisting of $CH_3$, $C_2H_5$, $OCH_3$, $OC_2H_5$, Cl, Br, OH, or $NH_2$:

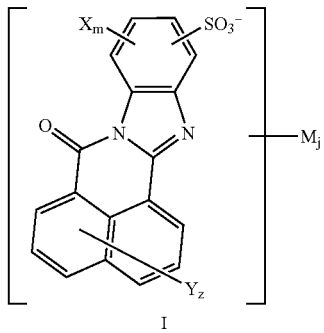

I where m is an integer in the range of
0 to 3, and z is an integer in the
range of 0 to 6;

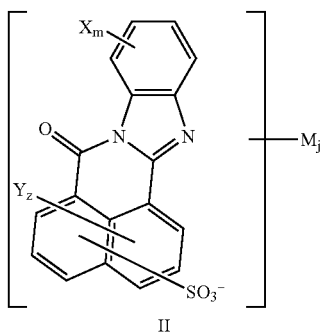

II where m is an integer in the range of 0
to 4, and z is an integer in the range of
0 to 5;

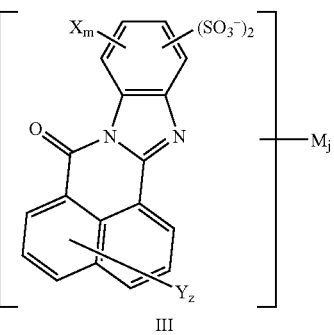

III where m is an integer in the range of
0 to 2, and z is an integer in the
range of 0 to 6;

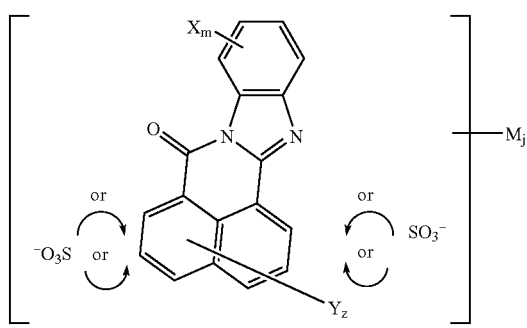

IV where m is an integer in the range of 0
to 4, and z is an integer in the range of
0 to 4;

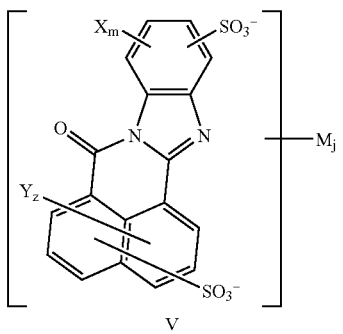

V where m is an integer in the range of
0 to 3, and z is an integer in the
range of 0 to 5;

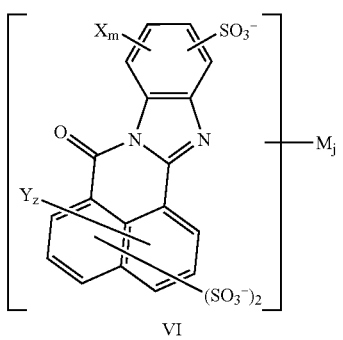

VI where m is an integer in the range of 0
to 3, and z is an integer in the range of
0 to 4;

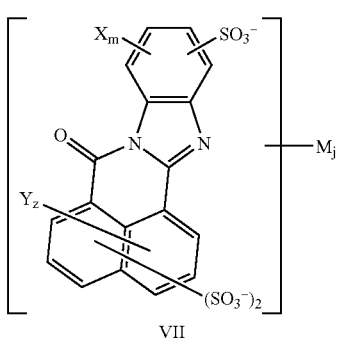

VII where m is an integer in the range of
0 to 2, and z is an integer in the
range of 0 to 5;

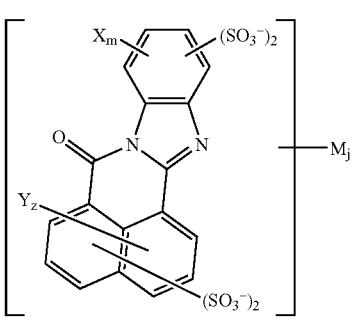

VIII where m is an integer in the range of 0
to 2, and z is an integer in the range of
0 to 4;

In an additional embodiment of the present invention, a lyotropic liquid crystal system is provided wherein the LLC is formed of a 1,8-Naphthoylene-1',2'-benzimidazole sulfoderivatives of the preceding embodiments.

In yet another embodiment of the present invention an optically anisotropic film is provided. This film comprises an individual 1,8-naphthoylene-1',2'-benzimidazole sulfoderivative according to the preceding embodiments.

In a further embodiment of the present invention, a method for forming an optically anisotropic film is provided. In this method, a liquid crystal system according to one of the embodiments described herein is deposited onto a substrate. An orienting force is applied and the film is dried.

BRIEF DESCRIPTION OF THE DRAWINGS

Other objects and advantages of the present invention will become apparent upon reading the detailed description of the invention and the appended claims provided below, and upon reference to the drawings, in which:

DETAILED DESCRIPTION OF THE INVENTION

Figure 1:
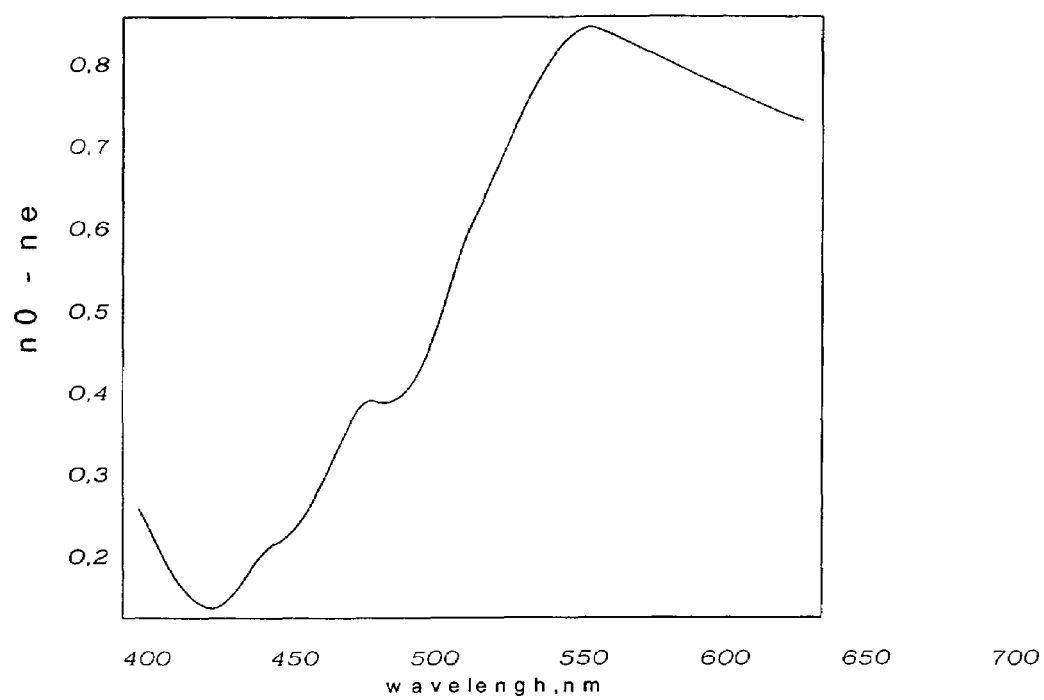
FIG. 1 is a chart plotting the spectral dependence of the degree of anisotropy for a film of naphthoylenebenzimidazole sulfoderivative according to the present invention.

The present invention provides new chemical compounds belonging to the class of 1,8-naphthoylene-1',2'-benzimidazole sulfoderivatives (sulfonates) as well as methods for their synthesis. These compounds are capable of forming stable LLC phases, and they have great potential utility as materials for use in the formation of optically anisotropic, at least partially crystalline films.

The invention is aimed at increasing the assortment of compounds that either do not or only weakly absorb light in the visible range of the electromagnetic spectrum. Compounds of the present invention are capable of forming stable LLC phases with increased stability. These materials may be used to for the obtaining of optically anisotropic, at least partially crystalline films that possess high optical characteristics and that avoid may disadvantages of previously available films.

In one embodiment of the present invention, weakly absorbing (slightly colored) films which can be used both as polarizing and phase-shifting (retarder) are provided. Methods for the synthesis of the compounds and for preparation of the films are also disclosed. Some compounds of the aroylenebenzimidazole series, namely 1,8-naphthoylene-1', 2'-benzimidazoles, possess a π-electron conjugation system that is not as developed as that of naphthalenetetracarboxylic or perylenetetracarboxylic acid benzimidazoles. For this reason, the 1,8-naphthoylene-1',2'-benzimidazoles of the present invention do not absorb in the UV and near visible spectral regions. In particular, unsubstituted 1,8-naphthoylene-1',2'-benzimidazole exhibits a maximum absorption at $\lambda$=380 nm.

Another embodiment of the present invention provides methods for the synthesis of new organic compounds that are capable of forming LLC phases possessing increased stability in a broad range of concentrations, temperatures, and pH values. These methods simplify the process of film formation, allow standard equipment to be employed for the application of layers, and facilitate production of films with reproducible parameters.

In yet another aspect of the present invention, new organic compounds are provided. These compounds may form solutions that are characterized by an optimum hydrophilic-hydrophobic balance that favorably influences the size and shape of supramolecular complexes formed in such systems, as a well as the degree of molecular order in these complexes. This characteristic provides the necessary solubility of the compounds under consideration in addition to enhancing stability of LLC phases based on these compounds. This, in turn, improves the reproducibility of the film parameters and simplifies the production technology because the requirements for selecting and maintaining the optimum technological conditions on various production stages are decreased. Optical characteristics of films based on these compounds are further enhanced because the molecules of 1,8-naphthoylene-1',2'-benzimidazole sulfoderivatives are characterized by increased homogeneity of the orientation of their planes and the dipole moments of electron transitions (lying in these planes) relative to the direction determined by an external orienting factor.

The 1,8-naphthoylene-1',2'-benzimidazole, water-soluble sulfoderivative compounds of the present invention are a novel improvement over previously disclosed materials used in the formation of anisotropic films. Compounds according to the disclosed invention are generally described by the structural formula:

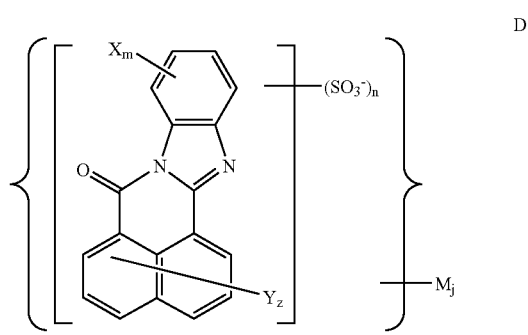

D where n is an integer in the range of 1 to 4; m is an integer in the range from 0 to 4; z is an integer in the range of 0 to 6; and m+z+n≦10; X and Y are individually selected from the group consisting of $CH_3$, $C_2H_5$, $OCH_3$, $OC_2H_5$, Cl, Br, OH, or $NH_2$;

M is a counterion; and j is the number of counterions in a dye molecule, which may be fractional if the counterion is shared among several molecules (for n>1, different counterions can be involved). Compounds described by general formula D include a number of structures that differ, for example, in the number and position of sulfonic groups and other substituents. Structures I–VIII below are exemplary, more specific embodiments of 1,8-Naphthoylene-1',2'-benzimidazole sulfoderivatives of the general formula D according to the present invention. These examples are not intended to restrict the scope of the present invention in any way.

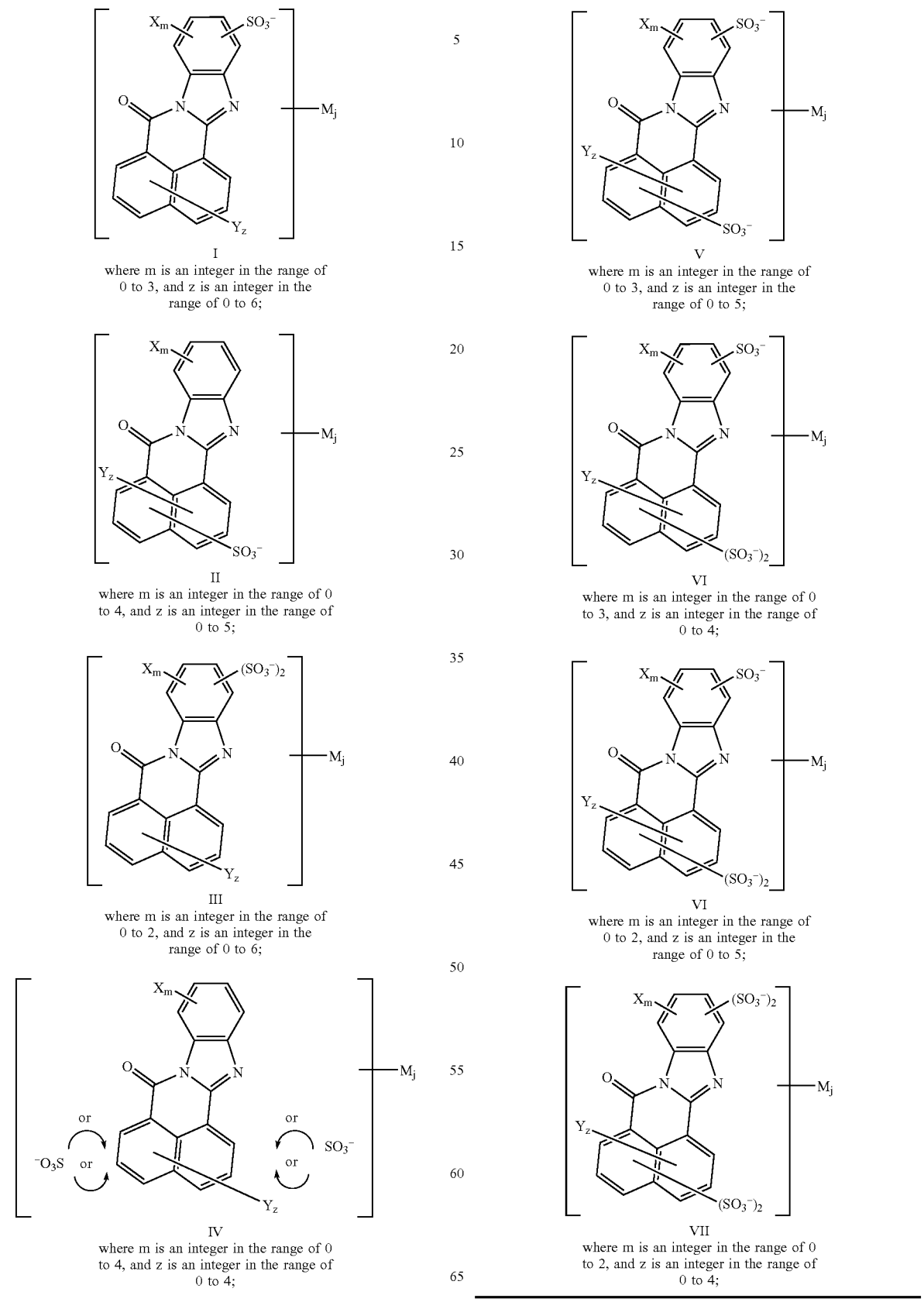

For structures I–VIII, X and Y are individually selected from the group consisting of $CH_3$, $C_2H_5$, $OCH_3$, $OC_2H_5$, Cl, Br, OH, or $NH_2$, M is a counterion; and j is the number of counterions in a dye molecule, which can be fractional if the counterion is shared among several molecules (when the number of sulfonic groups is greater than one (n>1), different counterions can be involved).

Compounds I–VIII as well as other compounds according to the present invention, are capable of forming stable LLC phases, both individually and in mixtures with other substances including other compounds according to the present invention, other dichroic dyes, and various colorless (or weakly absorbing in the visible range) organic compounds. After solvent removal, these LLC phases can form anisotropic, at least partially crystalline films possessing high optical characteristics. In structures I and II, counterions M include one or more cations selected from the series $H^+$, $NH_4^+$, $K^+$, $Li^+$, $Na^+$, $Cs^+$, $Ca^{2+}$, $Sr^{2+}$, $Mg^{2+}$, $Ba^{2+}$, $Co^{2+}$, $Mn^{2+}$, $Zn^{2+}$, $Cu^{2+}$, $Pb^{2+}$, $Fe^{2+}$, $Ni^{2+}$, $Al^{3+}$, $Ce^{3+}$, $La^{3+}$, etc., as well as by combinations of such cations.

Naphthoylenebenzimidazole sulfoderivatives according to the present invention exhibit maximum optical absorption in the near UV range (in the vicinity of 380 nm) in aqueous solutions. Introduction of substituents such as ethyl, methyl, chlorine, and bromine does not significantly shift the absorption band, while the introduction of amino and hydroxy groups leads to broadening of the absorption band and changes the character of the spectrum. By varying the number of sulfonic groups and the number and character of substituents in 1,8-naphthoylene-1',2'-benzimidazole molecules according to the present invention, it is possible to control the hydrophilic-hydrophobic balance of aggregates formed in liquid-crystalline solutions and to change the solution viscosity. However, the desirable aspects of the present invention may also be realized through other combinations of the aforementioned parameters and substituents.

Additional desirable results of the present invention may be obtained by using chemical compounds corresponding to one or more of the structural formulas disclosed herein, a lyotropic liquid crystal system based on these compounds, and related optically anisotropic films.

All the aforementioned 1,8-naphthoylene-1',2'-benzimidazole sulfoderivatives are capable of forming stable LLC phases. The 1,8-naphthoylene-1',2'-benzimidazole sulfoderivatives of the present invention are desirably used for manufacturing optically isotropic or anisotropic films. The 1,8-naphthoylene-1',2'-benzimidazole sulfoderivatives according to present invention may also be advantageously applied in the production of at least partially crystalline films. The 1,8-naphthoylene-1',2'-benzimidazole sulfoderivatives described herein also have applications as polarizing and/or birefringent films.

1,8-Naphthoylene-1',2'-benzimidazole sulfoderivatives of the present invention enter into the composition of optically isotropic or anisotropic, polarizing and/or birefringent films. The material of an optically isotropic or anisotropic film according to the present invention includes at least two compounds, at least with one of formulas I–VIII, containing at least two different substituents.

In an additional embodiment, the present invention features an aqueous liquid crystal system (sometimes also called water-based ink composition) that comprises an individual 1,8-naphthoylene-1',2'-benzimidazole sulfoderivative according to the above general structure D or more specifically according to any of the structures I–VIII or mixtures of these compounds.

In another embodiment, a liquid crystal system of the present invention is based on a mixture of water and an organic solvent that is either miscible with water in any proportion or characterized by limited miscibility with water. In this embodiment, the concentration of 1,8-naphthoylene-1',2'-benzimidazole sulfoderivatives, either individually or in a mixture, in the liquid crystal system is in the range of approximately 3% to 30% by mass. Alternatively, the concentration is in the range of approximately 7% to 15% by mass. The liquid crystal system of this embodiment further comprises up to approximately 5% by mass of surfactants and/or plasticizers. In this liquid crystal system the concentration of 1,8-naphthoylene-1',2'-benzimidazole sulfoderivatives may be within the following ranges, depending on the desired properties:

monosulfoderivatives of structures I and II with mass concentrations in the range of approximately 0 to 99 mass %, or alternatively in a mass concentration range of approximately 50 to 99%;

disulfoderivatives of structures III and IV with mass concentrations in the range of approximately 0 to 99 mass %, or alternatively in a mass concentration range of approximately 50 to 99%;

trisulfoderivatives of structures VI and VII with mass concentrations in the range of approximately 0 to 30 mass %, or alternatively in a mass concentration range of approximately 10 to 20%;

tetrasulfoderivatives of structure VIII with mass concentrations in the range of approximately 0 to 20 mass %, or alternatively in a mass concentration range of approximately 5 to 10%.

The liquid crystal system may further comprise at least one water-soluble organic dye or a colorless organic compound that is capable of participating in formation of a LLC phase. Alternatively, the liquid crystal system may further comprise at least two compounds from structures I–VIII and/or at least two compounds of at least one structure from I–VIII with at least two different substituents.

In another embodiment of the present invention, an optically isotropic film containing either individual 1,8-naphthoylene-1',2'-benzimidazole sulfoderivatives or a mixture of such compounds is provided. This optically anisotropic film may further comprise a different organic dye or some colorless compound. Exemplary organic dyes and colorless compounds that are capable of forming mixed liquid crystal systems with 1,8-naphthoylene-1',2'-benzimidazole sulfoderivatives include, but are not in any way limited to disodium chromoglyca:

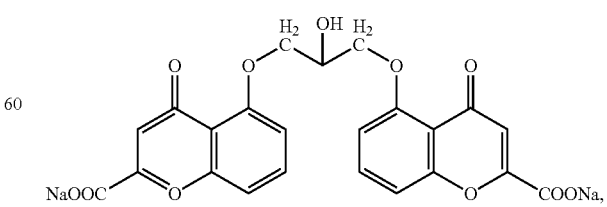

sulfoderivatives of phenanthrophenazine:

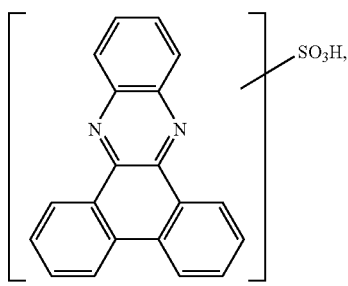

sulfoderivatives of naphthalenetetracarboxylic acid dibenzimidfazole:

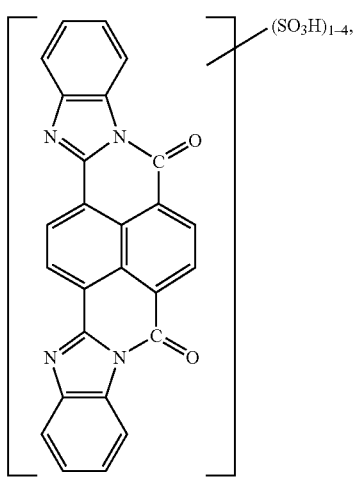

sulfoderivatives of perylenetetracarboxylic acid dibenzimidazole:

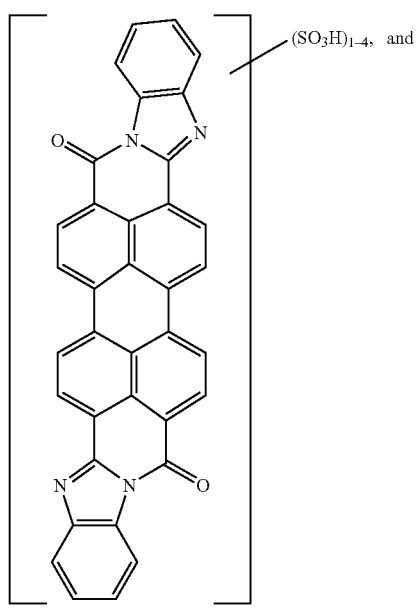

indanthrone sulfoderivatives

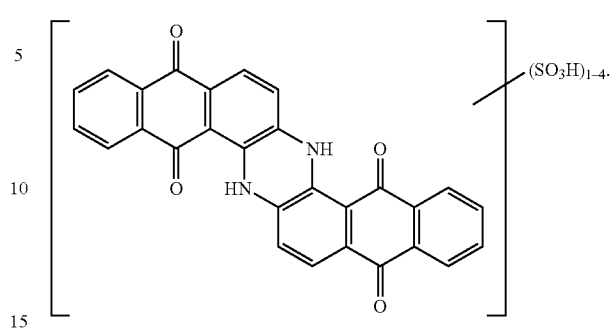

A wide variety of such compounds are available. The choice of particular additives for a given LLC system may be determined by one of skill in the art through routine experimentation based on the teachings herein and desired optical properties of the anisotropic films, rheological properties of the liquid crystal system, etc. The compound or compounds should be chosen such that introduction of the compound(s) does not cause breakage of the liquid crystal system. Optical polarization techniques may be used to monitor the impacts of a chosen additive to determine its suitability for use in a LLC according to the present invention.

An optically anisotropic film according to the present invention may be obtained by depositing a liquid crystal system onto a substrate, and by further applying orienting action and drying. In this embodiment, the anisotropic film is at least partially crystalline. The film material comprises at least two compounds of the structures I–VIII, and/or at least two compounds with one of structures I–VIII, with at least two different substituents.

The 1,8-naphthoylene-1',2'-benzimidazole sulfoderivatives according to the present invention as shown in structure D and more specifically in structures I–VIII with the general structural formulas may be synthesized by a variety of methods, both known and novel. Sulfoderivatives according to the present invention with the general formula X shown below are formed as a result of sulfonation of 1,8-naphthoylene-1',2'-benzimidazole or its derivatives IX with sulfuric acid or oleum of various concentrations in different temperature intervals according to the scheme:

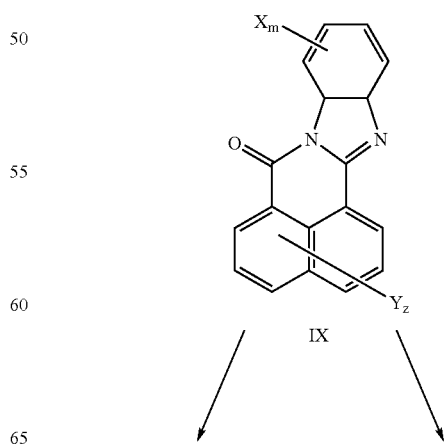

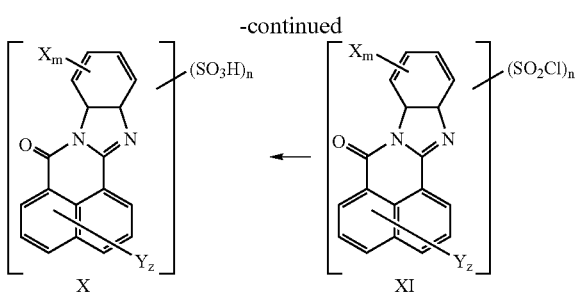

where n=1, 2, 3, 4; m=0, 1, 2, 3, 4; and z=0, 1, 2, 3, 4, so that m+z+n≦10; and X and Y are individually selected from the group consisting of $CH_3$, $C_2H_5$, $OCH_3$, $OC_2H_5$, Cl, Br, OH, and $NH_2$.

Sulfonates with the general formula X may be also obtained by hydrolysis of the corresponding derivatives XI, or formed as a result of sulfonation of compounds XI with chlorosulfonic acid as described in D. Tocksteinova, J. Slosar, J. Urbanek, and J. Churachek, *Microchim. Acta* 11, 193 (1979), or with the mixtures of chlorosulfonic acid with oleum of various concentrations. The sulfonation of 1,8-naphthoylene-1',2'-benzimidazole and its derivatives may be performed either in a medium of sulfonating agents or in organic solvents. In addition, 1,8-naphthoylene-1',2'-benzimidazole sulfoderivatives X can be synthesized by condensation of naphthalic acid anhydride or its derivatives XII with ortho-phenylenediamine or its derivatives XIII, provided that at least one of the initial compounds contains one or several sulfonic groups:

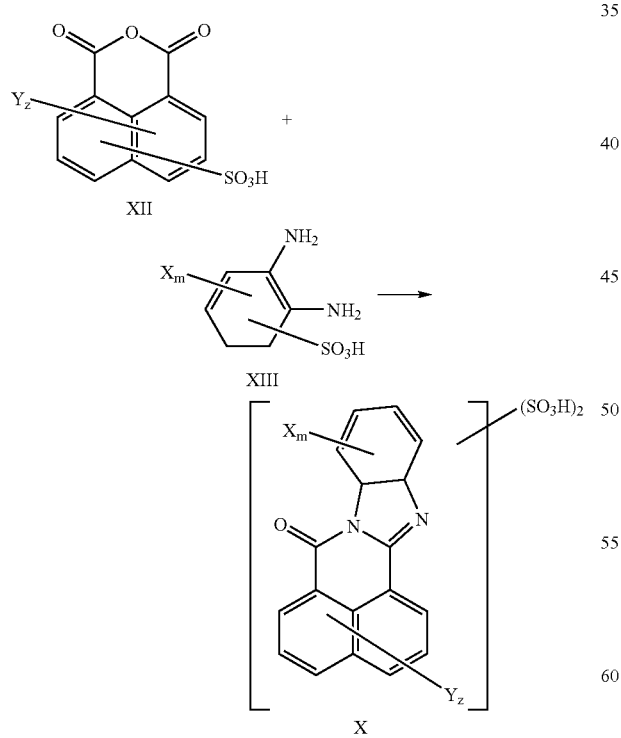

where m=0, 1, 2, 3, 4, and z=0, 1, 2, 3, 4, so that m+z≦7; and X and Y individually are selected from the group consisting of $CH_3$, $C_2H_5$, $OCH_3$, $OC_2H_5$, Cl, Br, OH, and $NH_2$. 1,8-naphthoylene-1',2'-benzimidazole sulfoderivatives may also be obtained by separating their mixtures through fractional precipitation from solutions.

Mixtures of 1,8-naphthoylene-1',2'-benzimidazole sulfoderivatives can be also obtained by isomerization, for example

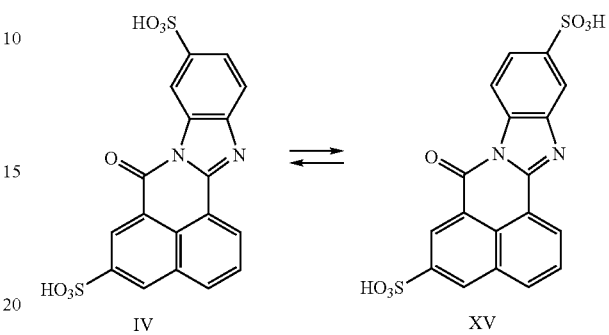

When compounds according to the present invention or mixtures thereof are dissolved in water, their molecules form anisometric (rodlike) aggregates packed similarly to coins in a stack. Each aggregate in such a solution represents a micelle with an electric double layer, while the entire solution represents a highly dispersed (colloidal) lyophilic system. As the solution concentration (i.e., micelle concentration) increases, the anisometric aggregates exhibit spontaneous ordering (self-ordering), leading to formation of a nematic lyotropic mesophase. As a result, the system becomes liquid-crystalline. The solution typically becomes a liquid crystal system at a concentration in the range of approximately 3% to 50% by mass, depending on the particular type and ratio of 1,8-naphthoylene-1',2'-benzimidazole sulfoderivatives. The liquid crystal state is readily verified by usual methods, for example, with the aid of a polarizing microscope.

Liquid crystal systems (solutions) based on the individual naphthalic acid benzimidazole sulfoderivatives of the present invention, i.e. structure D and more specifically structures I–VIII, or on mixtures of such compounds can be applied onto a substrate surface and oriented by previously described methods, such as for instance those disclosed in PCT publications WO 94/28073 and WO 00/25155. For example, orientation may be achieved by applying shear stress or gravitational or electromagnetic fields. To enhance substrate wetting and to optimize rheological properties of a liquid crystal system, the solution can be modified, for example, by adding plasticizing additives, such as for example water-soluble polymers, and/or anionic or nonionic surfactants. The system may also contain low-molecular-weight water-soluble additives. All additives are desirably selected so as not to violate orientation of the liquid crystal solution. Subsequent removal of the solvent from the oriented film leads to the formation of an optically anisotropic polycrystalline film with a thickness in the range of approximately 0.2 to 1.2 μm. In the visible spectral range (approximately 380–900 nm), a difference in the refractive indices measured in the direction of orientation and in the perpendicular direction occurs in the range of approximately 0.1–0.8. Such values are achieved with previously known retarders only at film thicknesses greater than approximately 200 μm. The efficiency of birefringent films according to the disclosed invention is 100–200 times or more higher than previously disclosed films.

Thus, 1,8-naphthoylene-1',2'-benzimidazole sulfoderivatives according to this invention are capable of forming LLC phases and ensure the obtaining of slightly colored (weakly absorbing in the visible range) anisotropic films possessing high optical characteristics.

Figure 2A:
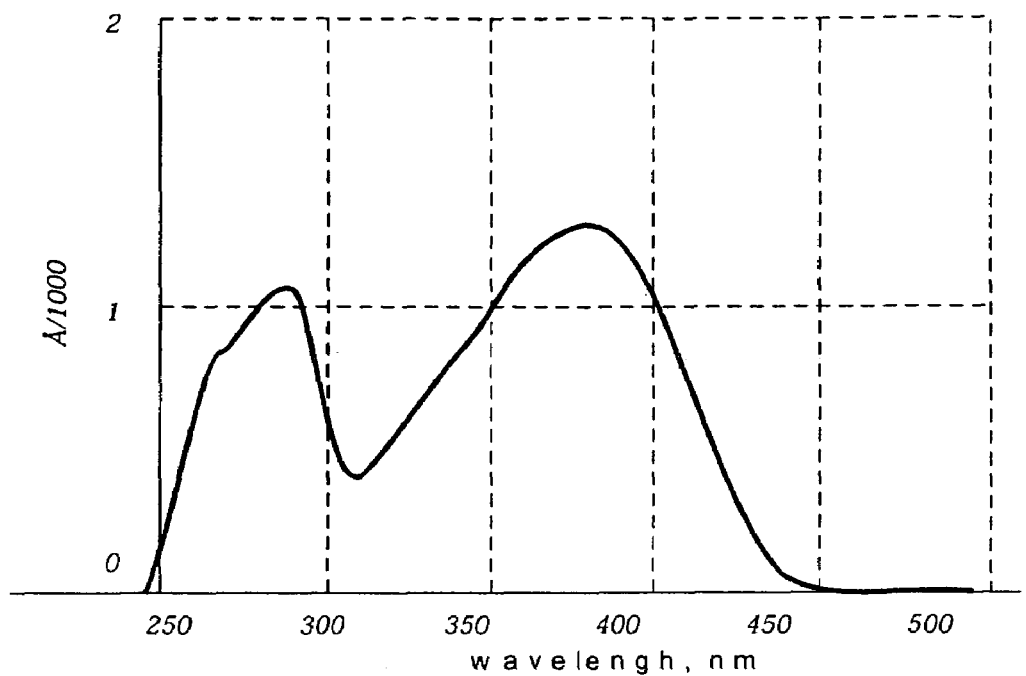
FIG. 2 is a chart plotting the electronic absorption spectra of (a) 1,8-naphthoylene-1',2'-benzimidazole-3,6'-disulfonic acid and (b) 1,8-naphthoylene-1',2'-benzimidazole-6'-amino-3-sulfonic acid according to the present invention.
Figure 2B:
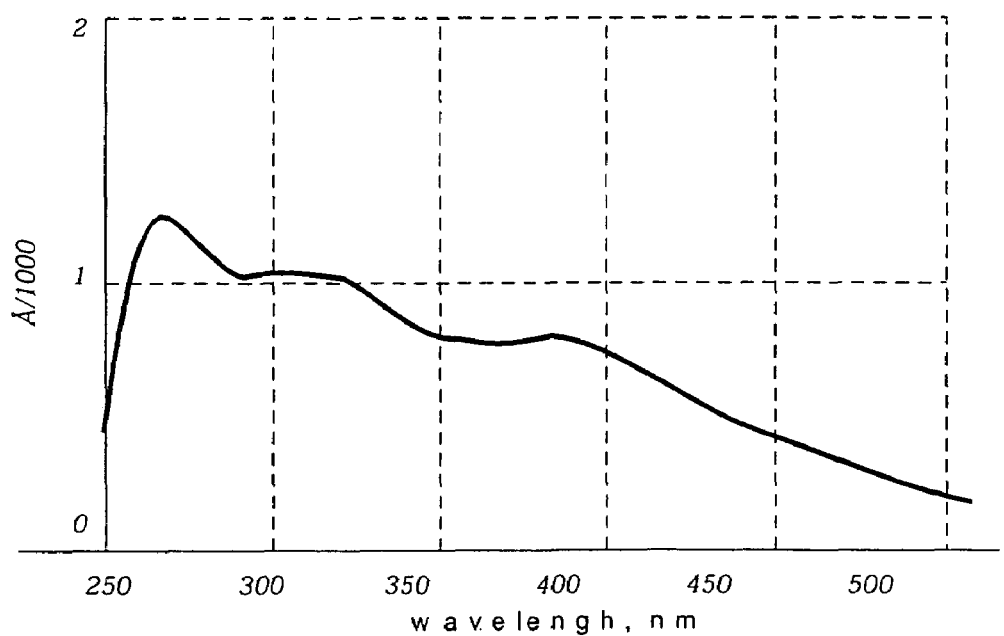

FIGS. 1–3 illustrate some of the advantages of the present invention. FIG. 1 shows the spectral dependence of the degree of anisotropy for a film of naphthoylenebenzimidazole sulfoderivative. FIG. 2 presents the electronic absorption spectra of (a) 1,8-naphthoylene-1',2'-benzimidazole-3,6'-disulfonic acid and (b) 1,8-naphthoylene-1',2'-benzimidazole-6'-amino-3-sulfonic acid. FIG. 3 shows the plots of (a) refractive index and (b) absorption coefficient versus wavelength for a film of 1,8-naphthoylene-1',2'-benzimidazole-6'-sulfonic acid.

EXPERIMENTAL

The synthesis of 1,8-naphthoylene-1',2'-benzimidazole sulfoderivatives according to this invention is illustrated by the following examples. These experiments are intended for illustration purpose only and are not intended to limit the scope of the present invention in any way.

Example I

Synthesis of 1,8-naphthoylene-1',2'-benzimidazole-6'-sulfonic acid via sulfonation of 1,8-naphthoylene-1',2'-benzimidazole was performed as follows. A mixture of 5.0 g of 1,8-naphthoylene-1',2'-benzimidazole and 30 ml of 10% oleum was stirred for 1.5 h. Then the reaction mass was diluted with water to obtain a 70% aqueous sulfuric acid solution. The precipitate was filtered, washed with hydrochloric acid until the absence of $SO_4^{2-}$ ions, and dried at 100° C. The yield of 1,8-naphthoylene-1',2'-benzimidazole-6'-sulfonic acid was 5.7 g (88%).

Analysis of the sample revealed the following data:
$^1$H NMR spectrum (Bruker AC-300) in DMSO δ, ppm: 7.78 (singlet, 2H), 7.95 (multiplet, 2H), 8.39 (doublet, 1H), 8.55 (doublet, 1H), 8.78 (multiplet, 3H).
Mass spectrum (VISION 2000, negative reflection mode): found, m/z=347.8; calculated., 350.35.
IR spectrum (FSM-1201 Fourier-transform spectrometer) in thin films on KRS-5 windows was (η, cm$^{-1}$): 653, 1070, 1234 ($SO_3H$); 1731.2 (C=O).
Electronic absorption spectrum (Ocean PC 2000 spectrophotometer) in aqueous solution ($λ_{max}$, nm): 380.
Elemental analysis measured (%): C 61.61, 61.60; H 2.67, 2.76; N 7.97, 8.12; S 9.32, 9.41; $C_{18}H_{10}N_2O_4S$. Calculated values were C, 61.71; H, 2.88; N 8.00; O 18.27; S 9.15.

Example 2

Synthesis of 1,8-naphthoylene-1',2'-benzimidazole-3,6'-disulfonic acid via sulfonation of 1,8-naphthoylene-1',2'-benzimidazole was performed as follows. A mixture of 3.0 g of 1,8-naphthoylene-1',2'-benzimidazole and 32 ml of 20% oleum was stirred at 50–55° C. for 4 h. Then the reaction mass was diluted with water so as to obtain a 52% aqueous sulfuric acid solution. The precipitate was filtered, washed with hydrochloric acid until the absence of $SO_4^{2-}$ ions, and dried at 100° C. The yield of 1,8-naphthoylene-1',2'-benzimidazole-3,6'-disulfonic acid is 4.3 g (90%).

$^1$H NMR spectrum (Bruker AC-300) in DMSO (δ, ppm): 7.82 (singlet, 2H), 7.97 (multiplet, 1H), 8.64 (doublet, 2H), 8.78 (doublet, 2H), 9.03 (singlet, 1H);

Analysis of the sample revealed the following data:
Mass spectrum (VISION 2000, negative reflection mode): found, m/z=428.8; calculated., 430.41;
Infrared (IR) spectrum (FSM-1201 Fourier-transform spectrometer) in thin films on KRS-5 windows (η, cm$^{-1}$): peaks were located at 653, 1070, 1234 ($SO_3H$), 731.2 (C=O) cm$^{-1}$.
The electron absorption spectrum (Ocean PC 2000 spectrophotometer) in aqueous solution had $λ_{max}$=380 nm.
Elemental analysis measured (%): C 50.11, 50.08; H 2.05, 2.24; N 6.46; 6.62; S 14.50, 14.63; $C_{18}H_{10}N_2O_7S_2$. Calculated values were C 50.23; H, 2.34; N, 6.51; O 26.02; S 14.90.

Example 3

Synthesis of 1,8-naphthoylene-1',2'-benzimidazole-3,6,6'-trisulfonic acid via sulfonation of 1,8-naphthoylene-1',2'-benzimidazole was performed as follows. A mixture of 1.5 g of 1,8-naphthoylene-1',2'-benzimidazole and 10 ml of 20% oleum was stirred at 115–120° C. for 14 h and cooled on ice. Then the reaction mass (kept on ice) was diluted with 10 ml of water at 17–20° C. and the mixture was allowed to stand for 24 h. The precipitate was filtered, washed with hydrochloric acid, and dried at 100° C. to constant weight. The yield of 1,8-naphthoylene-1',2'-benzimidazole-3,6,6'-trisulfonic acid is 1.1 g (40%).

Analysis of the sample revealed the following data:
$^1$H NMR spectrum (Bruker AC-300) in DMSO (δ, ppm): 7.82 (singlet, 2H), 8.62 (singlet 1H), 8.77 (doublet, 2H), 8.90 (singlet, 1H), 9.00 (singlet, 1H);
Mass spectrum (VISION 2000, negative reflection mode) measured m/z=509.1; calculated value was 510.48.
IR spectrum (FSM-1201 Fourier-transform spectrometer) in thin films on KRS-5 windows (η, cm$^{-1}$): 653, 1070, 1234 (SO3H), 1731.2 (C=O).
Electronic absorption spectrum (Ocean PC 2000 spectrophotometer) in aqueous solution measured $λ_{max}$=380 nm. Elemental analysis measured (%): C 42.15; 42.46; H 2.13, 2.06; N 5.22, 5.37; S 19.01, 19.16; $C_{18}H_{10}N_2O_{10}S_3$. Calculated value was C, 42.35; H, 1.97; N, 5.49; O 31.34; S 18.84.

Example 4

Synthesis of 1,8-naphthoylene-1',2'-benzimidazole-6'-sulfonic acid via condensation of ortho-phenylenediamine and 3-sulfonaphthalic acid anhydride.

A mixture of 2.3 g of 3-sulfonaphthalic acid anhydride and 1.4 g of ortho-phenylenediamine in 50 ml of acetic acid was boiled for 8 h and cooled to 15° C. The precipitate was filtered, washed with acetic acid cooled to 15° C., and dried to obtain 2.3 g of a mixture of isomeric 1,8-naphthoylene-1',2'-benzimidazole-3-sulfonic and 1,8-naphthoylene-1',2'-benzimidazole-6-sulfonic acids.

A similar procedure can be used to obtain other 1,8-naphthoylene-1',2'-benzimidazole sulfoderivatives containing various substituents.

Example 5

Synthesis of a liquid-crystalline composition, application of an optically anisotropic film, and determination of the optical characteristics of the film was performed as follows. A solution of 12 g of 1,8-naphthoylene-1',2'-benzimidazole-6'-sulfonic acid prepared with stirring at 20° C. in 65.0 g of deionized water was added 5.3 ml of a 25% aqueous ammonia and the mixture was stirred until complete dissolution. To this solution was added 10 g of a 1% sulfonol solution and the mixture was thoroughly stirred to obtain 92 g of a 13% liquid-crystalline solution. This solution was applied onto a glass plate with a Meyer rod at a rate of 25 mm/s. The process was conducted at a temperature of 20° C. and a relative humidity of 65%, after which the film was dried under the same conditions.

Figure 3A:
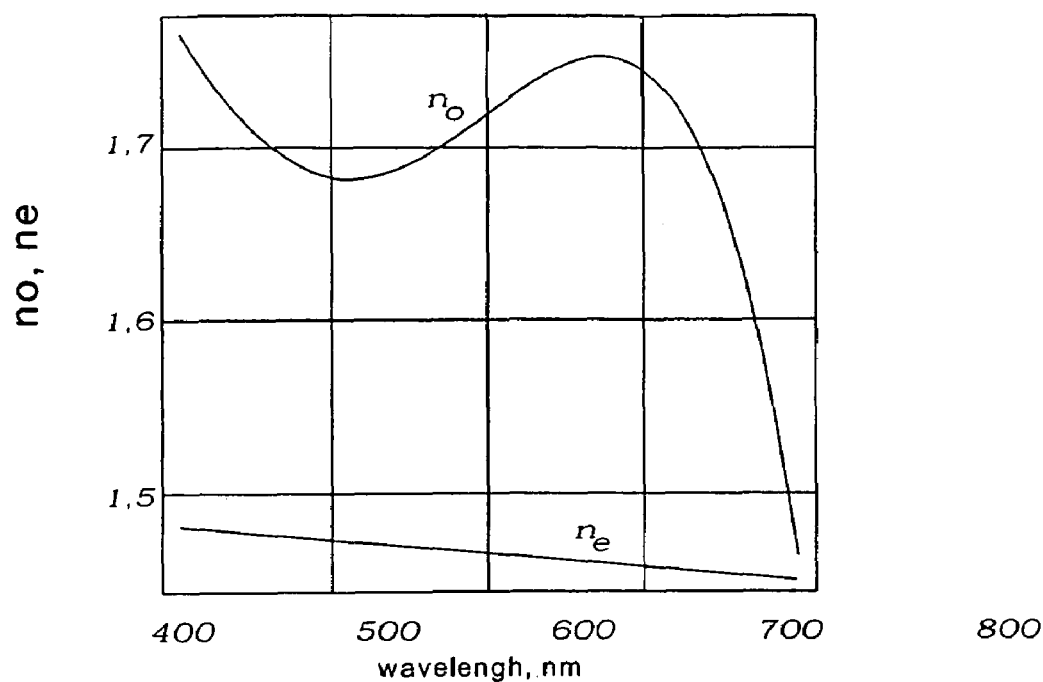
FIG. 3 is a chart plotting the (a) refractive index and (b) absorption coefficient versus wavelength for a film of 1,8-naphthoylene-1',2'-benzimidazole-6'-sulfonic acid according to the present invention.
Figure 3B:
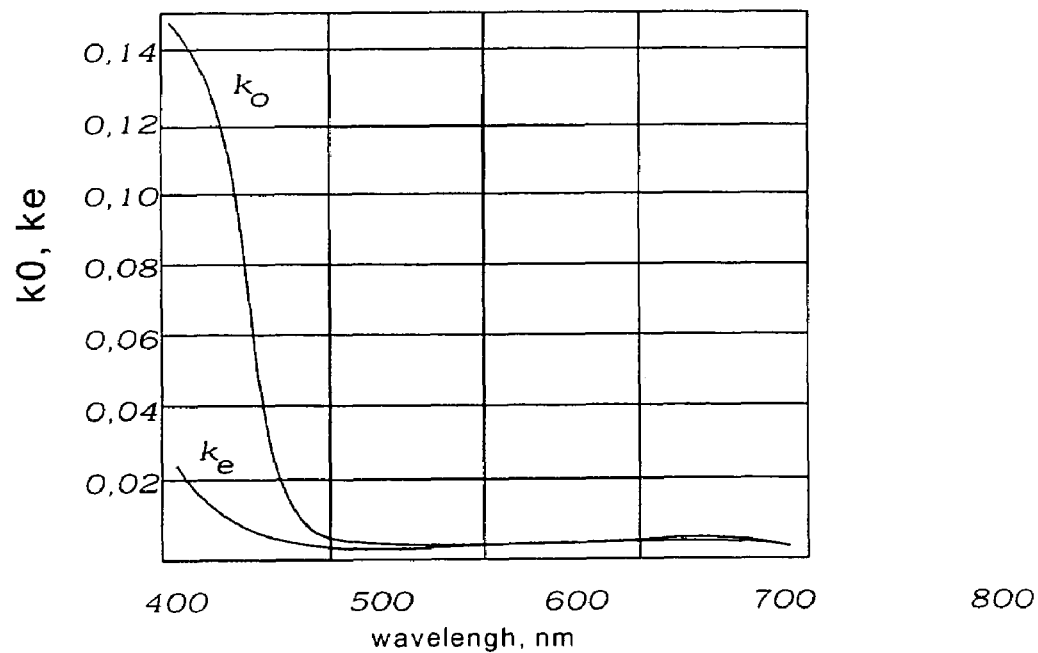

The optical properties of the films were studied by measuring the transmission spectra of the samples in a wavelength range from 400 to 800 nm (Cary 500 spectrophotometer) using a light beam polarized along the direction of film application and in the perpendicular direction. The measurements were also performed at an angle of 30° relative to the polarization plane normal. The results of these measurements were used to calculate the refractive indices ($n_o$, $n_e$) and the absorption coefficients ($k_o$, $k_e$) in the directions along and across the direction of film application. The method of calculation is described elsewhere [P. Lazarev, N. Ovchinnikova, and M. Paukshto, Submicron Film Retardation Coating, *SID '01 DIGEST* (San Jose, Calif., June 2001), Vol. XXXII, p. 571]. The results of calculations for a film of 1,8-naphthoylene-1',2'-benzimidazole-6'-sulfonic acid are presented in FIG. 3. The film is optically anisotropic, shows good phase-shifting properties, as illustrated in FIG. 3a, possesses high polarization characteristics in the wavelength region of 380–450 nm, and exhibits very low absorption in the entire visible range above 500 nm, as shown in FIG. 3b.

Lyotropic liquid crystal systems and the corresponding films were obtained for all other compounds described above. The optical characteristics of these films were also high, that supports the technical result of the disclosed invention.

The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents.

What is claimed is:

1. A 1,8-naphthoylene-1',2'-benzimidazole sulfoderivative of the general structural formulae:

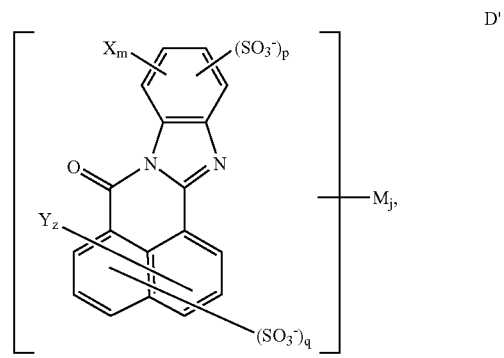

wherein:
p is an integer in the range of 1 to 2;
q is an integer in the range of 1 to 2;
m is an integer in the range of 0 to 4;
z is an integer in the range of 0 to 6, such that values of m, z, p and q satisfy the equation m+z+p+q≦10;
X and Y are individually selected from the group consisting of $CH_3$, $C_2H_5$, $OCH_3$, $OC_2H_5$, Cl, Br, OH, and $NH_2$;
M is a counterion; and
j is the number of said counterion in a single molecule of said 1,8-naphthoylene-1',2'-benzimidazole sulfoderivative, or:

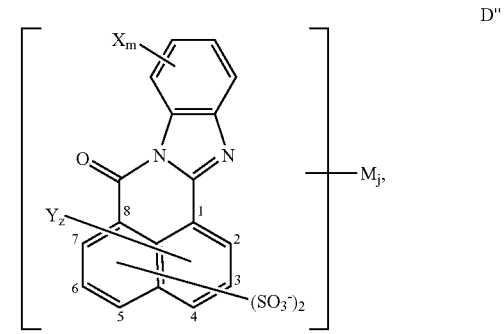

wherein at least one of the sulfonic groups occupies position 2, 3, 6 or 7;
m is an integer in the range of 1 to 4;
z is an integer in the range of 0 to 4;
X and Y are individually selected from $NH_2$ and/or OH;
M is a counterion; and
j is the number of said counterions.

2. The 1,8-naphthoylene-1',2'-benzimidazole sulfoderivative of claim 1 wherein the structural formula is chosen from the group consisting of structures IV–VIII:

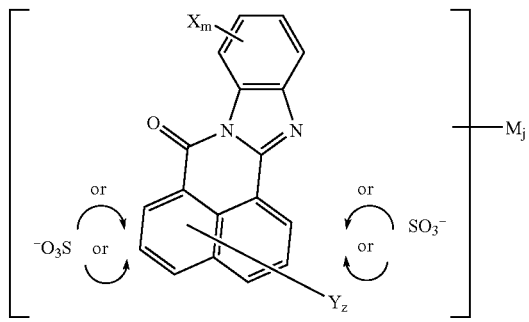

IV where m is an integer in the range of 0 to 4, and z is an integer in the range of 0 to 4;

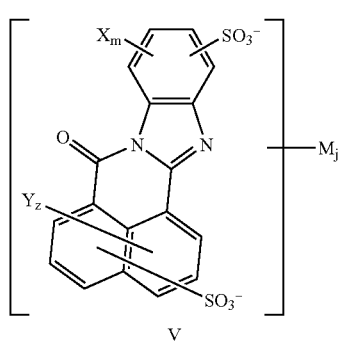

V where m is an integer in the range of 0 to 3, and z is an integer in the range of 0 to 5;

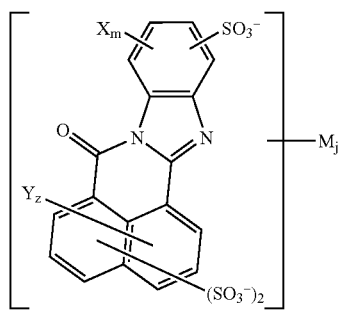

VI where m is an integer in the range of 0 to 3, and z is an integer in the range of 0 to 4;

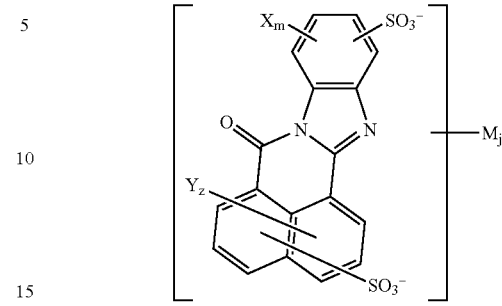

VII where m is an integer in the range of 0 to 2, and z is an integer in the range of 0 to 5;

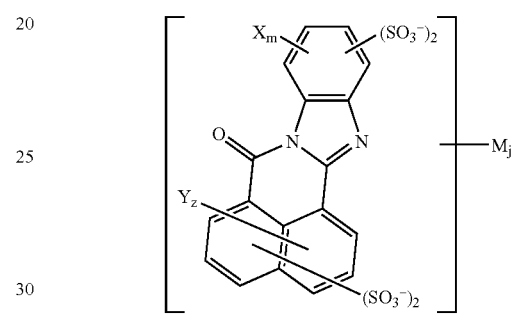

VIII where m is an integer in the range of 0 to 2, and z is an integer in the range of 0 to 4;

and X and Y are individually selected from the group consisting of $CH_3$, $C_2H_5$, $OCH_3$, $OC_2H_5$, Cl, Br, OH, and $NH_2$.

3. The 1,8-naphthoylene-1',2'-benzimidazole sulfoderivative according to claims 1 or 2, wherein:

said counterion (M) is shared among several molecules; and number of said counterions (j) is fractional.

4. The 1,8-naphthoylene-1',2'-benzimidazole sulfoderivative of claim 1 or 2 wherein said 1,8-naphthoylene-1',2'-benzimidazole sulfoderivative forms a stable lyotropic liquid crystal system.

* * * * *